United States Patent
Kim et al.

(10) Patent No.: US 9,433,234 B2
(45) Date of Patent: Sep. 6, 2016

(54) COMPOSITION FOR ODOR REMOVAL COMPRISING CUCURBITURIL

(71) Applicant: POSTECH ACADEMY-INDUSTRY FOUNDATION, Pohang-si, Gyeongsangbuk-do (KR)

(72) Inventors: Kimoon Kim, Pohang-si (KR); Young Ho Ko, Pohang-si (KR); Su Hyun Lee, Pohang-si (KR); Selvapalam Narayanan, Pohang-si (KR); Don Wook Lee, Pohang-si (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 14/443,354

(22) PCT Filed: Nov. 15, 2013

(86) PCT No.: PCT/KR2013/010436
§ 371 (c)(1),
(2) Date: May 15, 2015

(87) PCT Pub. No.: WO2014/077642
PCT Pub. Date: May 22, 2014

(65) Prior Publication Data
US 2015/0314027 A1  Nov. 5, 2015

(30) Foreign Application Priority Data

Nov. 16, 2012 (KR) .................. 10-2012-0130352
Mar. 19, 2013 (KR) .................. 10-2013-0029323

(51) Int. Cl.
A61L 9/01 (2006.01)
A23L 1/015 (2006.01)
C07D 487/22 (2006.01)

(52) U.S. Cl.
CPC .............. *A23L 1/0156* (2013.01); *A61L 9/01* (2013.01); *C07D 487/22* (2013.01)

(58) Field of Classification Search
None
See application file for complete search history.

(56) References Cited

U.S. PATENT DOCUMENTS 6,869,466 B2 * 3/2005 Day .................. C07D 487/22
                                                      95/205
2002/0133003 A1  9/2002 Kim et al.
(Continued)

FOREIGN PATENT DOCUMENTS

| JP | 09-313582 A | 12/1997 |
|---|---|---|
| KR | 10-0400082 B1 | 9/2003 |
| KR | 10-2007-0073225 A | 7/2007 |
| KR | 10-2009-0003254 A | 1/2009 |
| WO | 00/68232 A1 | 11/2000 |

OTHER PUBLICATIONS

Kim et al. "Functionalized curcurbiturils and their applications", Chemical Society Reviews, Nov. 7, 2006, vol. 36, pp. 267-279.*
(Continued)

*Primary Examiner* — Robert A Wax
*Assistant Examiner* — Melissa Mercier
(74) *Attorney, Agent, or Firm* — Knobbe Martens Olson & Bear LLP (57) ABSTRACT

Disclosed herein is a composition for removing odor, the composition including cucurbituril. The composition can capture and remove various kinds of odor materials (particularly, ammonium ion-containing bad odor, such as a fishy smell or the like) because cucurbituril can interact with various odor materials using its hydrophobic cavity and both inlets covered with carbonyl groups. Therefore, this composition can be practically applied to the cleaning of air and the improvement of an environment.

7 Claims, 6 Drawing Sheets

(56) References Cited

U.S. PATENT DOCUMENTS

2003/0140787 A1 7/2003 Day et al.
2007/0154553 A1 7/2007 Kim et al.
2010/0028232 A1 2/2010 Bedell

OTHER PUBLICATIONS

International Search Report dated Feb. 5, 2014 of corresponding PCT/KR2013/010436 which is the parent application—3 pages.

Kim et al., 'Functionalized cucurbiturils and their applications', Chemical Society Reviews, Nov. 7, 2006, vol. 36, pp. 267-279.

Kim et al., "New Cucurbituril Homologues: Syntheses, Isolation, Characterization, and X-ray Crytal Structures of Cucurbit [n]uril (n=5, 7, and 8)", Journal of American Chemical Society, 2000, vol. 122, pp. 540-541.

Freeman et al., "Cucurbituril", Journal of American Chemical Society, 1981, vol. 103, p. 7367.

* cited by examiner

COMPOSITION FOR ODOR REMOVAL COMPRISING CUCURBITURIL

TECHNICAL FIELD

The present invention relates to a composition for removing an odor, the composition including cucurbituril, and a method of preparing the same.

BACKGROUND ART

There are many odor removing methods. For example, there are methods which use a material to block a receptor of an olfactory organ, methods whereby an odor material is oxidized, methods of removing odor-generating bacteria, methods that use a strong fragrant material, and methods of capturing an odor molecule using a porous material such as zeolite, silica or the like. Among these methods, the method of capturing an odor molecule using a porous material is efficient, but it is difficult to incorporate and apply this method in the form of spray. Therefore, recently, macrocylclic molecules that have water-soluble properties and can capture odor molecules have attracted considerable attention. Cyclodextrin is a typical example of such macrocyclic molecules. Cyclodextrin was discovered in 1891 and has been actively researched ever since it was discovered that cyclodextrin reacts with several compounds to form inclusion complexes. Thus, cyclodextrin has been utilized in various fields such as food manufacture, medicine and the like.

Meanwhile, cucurbit[6]uril is another type of macrocyclic compounds composed of six monomers and its structure was analyzed by X-ray crystallography (J. Am. Chem. Soc. 1981, 103, 7367). Later, in 2000, K. Kim and others synthesized and separated cucurbit[n]urils (n=5, 7, 8), as homologues of cucurbit[6]uril, as well as cucurbit[6]uril, by improving a conventional method of synthesizing cucurbit [6]uril, and their structures were analyzed by X-ray crystallography (J. Am. Chem. Soc. 2000, 122, 540). Meanwhile, International Patent Application Publication No. WO 00/68232 discloses cucurbit[n]uril which is represented by Chemical Formula below:

[Chemical Formula]

wherein n is an integer of 4 to 12.

Each of the cucurbituril derivatives is a compound composed of glycoluril monomers having no substituent group (KR-A-10-2007-0073225).

It is proposed in the prior patent of the present inventors that cucurbituril can be used as a bad odor remover or the like because it has a structure which can be associated with an organic compound. However, experiments that may support this possibility have never been carried out by the present inventors or other researchers. Thus, the present inventors experimentally found that cucurbituril can fulfill a function of removing an odor, and the present inventors also found the optimal composition ratio of the complex and the optimal conditions required to exhibit functions. Based on these findings, the present invention was completed.

DISCLOSURE

Technical Problem

Accordingly, the present invention has been devised to solve the above-mentioned problems, and an object of the present invention is to provide a composition for removing an odor, the composition including cucurbituril, which can effectively remove odors caused by various kinds of materials.

However, an object to be accomplished by the present invention is not limited to the above-mentioned object, and other objects (not mentioned) will be clearly understood from the following descriptions by those skilled in the art.

Technical Solution

In order to accomplish the above object, an aspect of the present invention provides a composition for removing an odor, the composition including a compound represented by Chemical Formula 1 below:

[Chemical Formula 1]

wherein n is an integer of 4 to 20, and X is O, S or NH, and wherein the composition includes 45 to 100 wt % of the compound of Chemical Formula 1 of n=7.

The compound of Chemical Formula 1 is cucurbituril.

Advantageous Effects

The composition of the present invention can capture and remove various kinds of odor materials (particularly, ammonium ion-containing bad odor, such as a fishy smell or the like) because cucurbituril can interact with various odor materials using its hydrophobic cavity and both inlets covered with carbonyl groups. Further, since the composition can effectively remove odors from various odor emission materials according to the composition ratio of cucurbituril homologues, it can be made into various products by suitably adjusting the composition ratio of cucurbituril homologues.

DESCRIPTION OF DRAWINGS

The above and other objects, features and advantages of the present invention will be more clearly understood from the following detailed description taken in conjunction with the accompanying drawings, in which.

EMBODIMENTS

Hereinafter, embodiments of the present invention will be described in detail with reference to the attached drawings.

The present invention provides a composition for removing odor, the composition including a compound represented by Chemical Formula 1 below:

[Chemical Formula 1]

wherein n is an integer of 4 to 20, and X is O, S or NH, and wherein the composition includes 45 to 100 wt % of the compound of Chemical Formula 1 of n=7.

The compound of Chemical Formula 1 is cucurbituril.

According to the experiment of the present inventors (refer to Example 1), since the cavity of cucurbit[7]uril, which is the compound of Chemical Formula 1 of n=7, is most easily associated with a fragrant material, cucurbit[7]uril is most advantageous in terms of removing an odor. In this case, it is preferred that the ratio of the amount of cucurbit[7]uril to the total amount of cucurbituril be high. However, in order to increase the amount of cucurbit[7]uril at the time of synthesizing cucurbit[7]uril, a process of purifying the synthesized cucurbit[7]uril (crude cucurbit[7]uril) is additionally required, thus decreasing economical efficiency. Therefore, the synthesized crude cucurbit[7]uril itself can be used to remove an odor, and, in this case, the amount of cucurbit[7]uril in the crude cucurbit[7]uril may be 45% to 100% based on the total amount of cucurbituril. The composition may further include cucurbiturils of Chemical Formula 1 of n=4 to 6 and 8 to 20 in an amount of 0~35%. Among the cucurbiturils of Chemical Formula 1 of n=4 to 6 and 8 to 20, cucurbit[6]uril is mostly used. Besides, the composition may further include cucurbiturils of Chemical Formula 1 of n=4, 5 and 8 to 20 in an amount of 0~5%.

The crude cucurbit[7]uril is synthesized by a method including the following steps. However, the synthesis method thereof is not limited thereto.

1) Glycoluril 1.05 M (150 g) and paraformaldehyde 2.2 M (67 g) are mixed with a sufficient amount of HCl (225 mL), and this mixture is heated to 85~90° C. for 18 hours to obtain a cucurbituril solution.

2) $H_2O$ (3 L) is added to the cucurbituril solution, and then the solution is filtered to obtain a filtrate, and then the filtrate is mixed with methanol (2.4 L) to obtain a solid-containing solution.

3) The solid-containing solution is filtered by a filter paper to obtain a solid compound, and then the solid compound is washed with methanol (2 L) and dried to obtain crude cucurbit[7]uril.

According to another embodiment of the present invention, the cucurbituril may be dissolved in a buffer. Examples of the buffer may include, but are not limited to, PBS (phosphate buffered saline), Tris-HCl, Tricine, HEPES (4-(2-hydroxyethyl)-1-piperazineethanesulfonic acid), MOPS (3-(N-morpholino)propanesulfonic acid), SSC (saline sodium citrate), and MES (2-(N-morpholino)ethanesulfonic acid).

The composition of the present invention may further include an additive. In this case, examples of the additive may include, but are not limited to, fragrances such as ethyl butyrate, camphor, menthol, hexanal, eugenol, citronellol, linalool, patchoulol, santalol, phenyl ethyl alcohol, terpineol, vanillin, benzaldehyde, methyl salicylate, isoamyl acetate, d-limonene, L-limonene, α-pinene, 2-hydroxy-p-cymene, methyl acetophenone, and cis-jasmone; and/or solvents such as cyclohexane, hexane, heptane, isooctane, isopentane, pentane, dimethyl ether, diethyl ether, methanol, ethanol, propanol, isopropanol, butanol, acetone and propellants.

The composition of the present invention is very effective at capturing an odor molecule having an amino group or a carboxyl group, but can effectively capture other odor molecules. The odor which can be removed by the composition of the present invention may be emitted from an odor emission material such as onion, garlic, pork, fish, fermented fish, mold, bacteria, body fluids, leather, sewage, industrial wastewater or the like. However, the kinds of the odor emission material are not limited thereto.

The composition of the present invention can remove an odor from an odor emission material by 30% or more, which was measured by an odor measuring device.

Cucurbituril, which is a macrocyclic compound, has a hydrophobic cavity, and has hydrophilic inlets at both sides thereof. Therefore, hydrophobic interaction occurs in the cavity of cucurbituril, and hydrogen bonding, polar interaction, cation-polar interaction and the like occur at the upper and lower inlets thereof at which six carbonyl groups are located, so cucurbituril exhibits inclusion effects using extremely stable noncovalent binding with various kinds of compounds. Particularly, cucurbituril is formed into a complex by extremely stable noncovalent binding with compounds having a functional group such as an amino group, a carboxyl group or the like. Thanks to it having such characteristics, cucurbituril can effectively capture various kinds of odor molecules, and thus cucurbituril can be used a deodorizer which is superior compared to conventional deodorizers.

In Example 1, an odor removing effect was evaluated using a mixture of cucurbituril homologues, and in Examples 2 and 3, the odor removing effect of each cucurbituril was compared to that of a commercially available deodorizer.

The odor removing effects in Examples may be different from each other according to the amount of an odor material, the kind of the odor material and the used portion of the odor material (for example, the degree of odor of onion is different with respect to each portion). The values (Y axis in graph) measured by an odor measuring device used in the experiment are relative values indicating the degree of strength and weakness of odor, so it is difficult to indicate these values as absolute values. Therefore, the comparison of the odor removing effect of each cucurbituril or each deodorizer may be regarded independently.

Hereinafter, the present invention will be described in more detail with reference to the following Examples. However, these Examples are set forth to illustrate the present invention, and the scope of the present invention is not limited thereto.

EXAMPLES

Example 1

Figure 1:
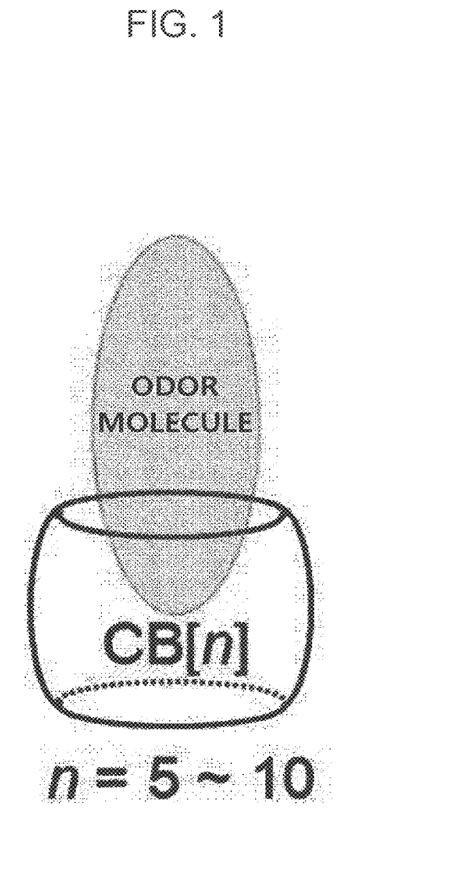
FIG. 1 is a schematic view showing a complex of cucurbituril and an odor molecule.
Figure 2A:
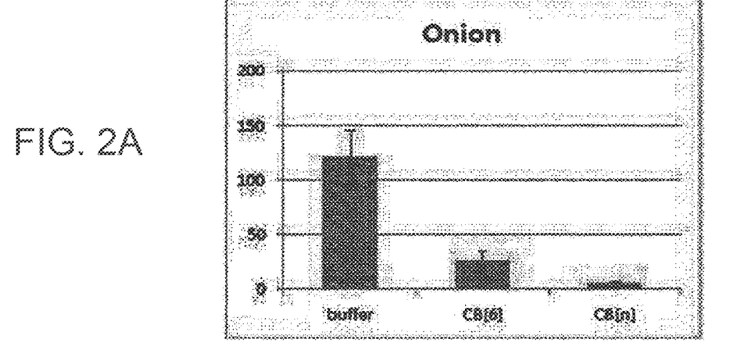
FIG. 2A is a graph showing the effect of removing the odor of onion using cucurbituril.
Figure 3A:
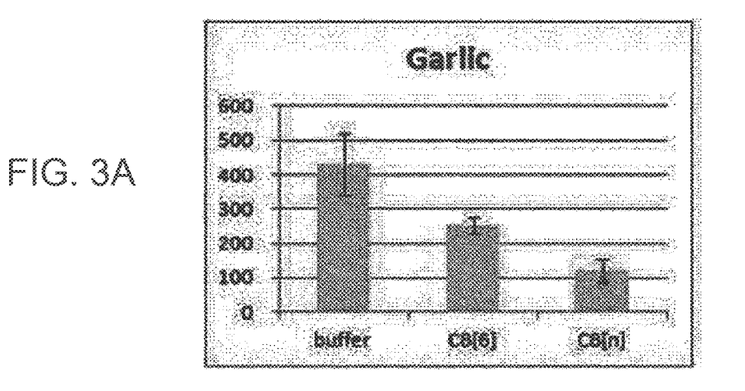
FIG. 3A is a graph showing the effect of removing the odor of garlic using cucurbituril.
Figure 4A:
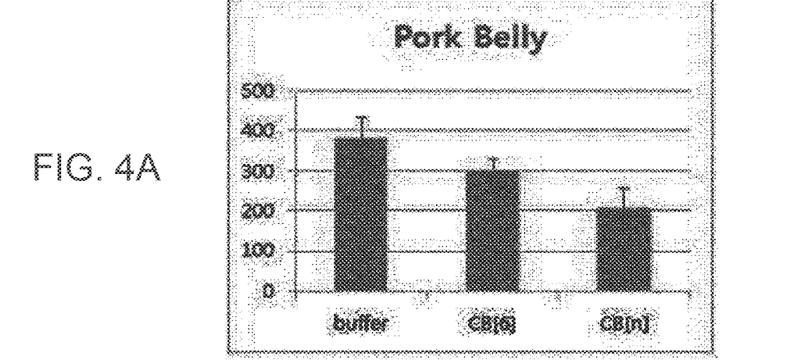
FIG. 4A is a graph showing the effect of removing the odor of pork belly using cucurbituril.
Figure 5A:
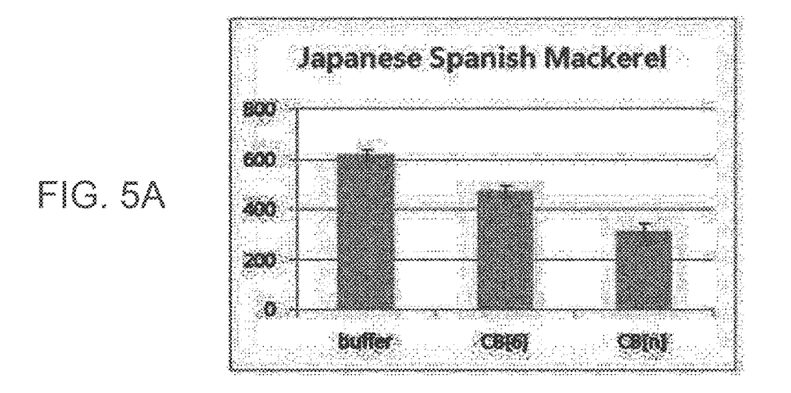
FIG. 5A is a graph showing the effect of removing the odor of a japanese spanish mackerel using cucurbituril.
Figure 6A:
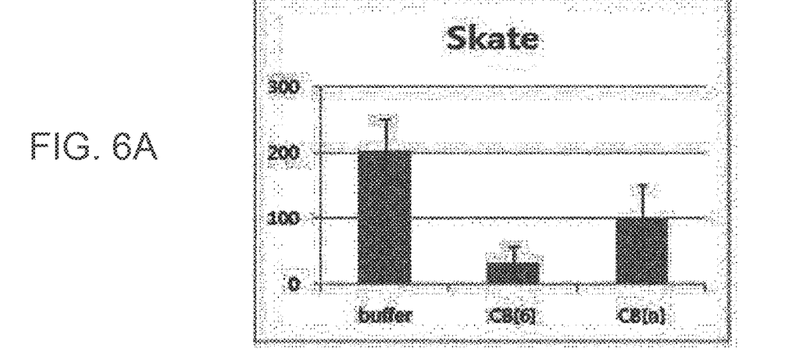
FIG. 6A is a graph showing the effect of removing the odor of a fermented skate using cucurbituril.

Preparation of Odor Removing Composition Including Cucurbituril and Evaluation of Odor Removing Effect Thereof Cucurbit[6]uril (CB[6]) and a mixture of cucurbituril homologues (CB[n], composition ratio: CB[5]:CB[6]:CB[7]:CB[8]=12.5%: 52.0%: 25.6%: 9.4%) were respectively dissolved in a buffer (PBS, pH 7.2) to obtain a solution (1 w/v %). The solution was sprayed onto odor emission materials such as onion, garlic, pork (pork belly), fish (japanese spanish mackerel), fermented fish (sliced raw skate) and the like to such a degree that each of the odor emission materials was sufficiently impregnated with the solution. After 1 hour, the degree of odor emission was measured using an odor measuring device (COSMOS, XP-329 m). The degree of reduction of odor emission was evaluated by the values measured by the odor measuring device on the basis of that obtained when only PBS buffer was sprayed. The average and standard deviation of the values obtained by testing the same sample three times were calculated and charted. The results thereof are shown in FIGS. 2A, 3A, 4A, 5A and 6A.

Example 2

Preparation of Odor Removing Composition Including Cucurbituril and β-Hydroxypropyl Cyclodextrin and Evaluation of Odor Removing Effect Thereof In order to compare the odor removing effect of each cucurbituril homologue with that of β-hydroxypropyl cyclodextrin, which is generally used as a deodorizer for textile materials, the following experiment was carried out.

Figure 2B:
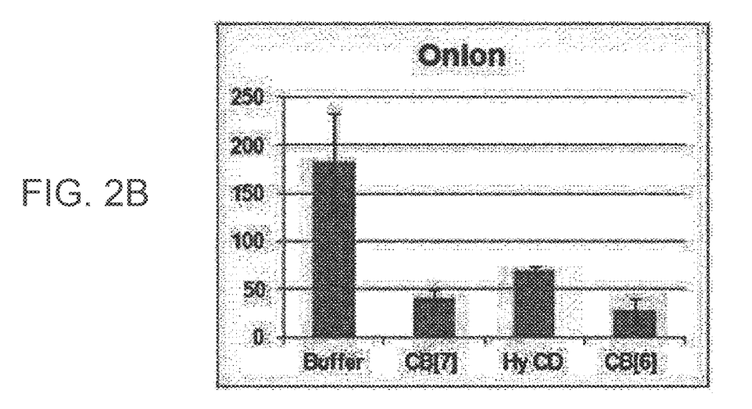
FIG. 2B is a graph showing the effect of removing the odor of onion using beta-hydroxypropyl cyclodextrin (HY CD, deodorizer) and cucurbituril.
Figure 3B:
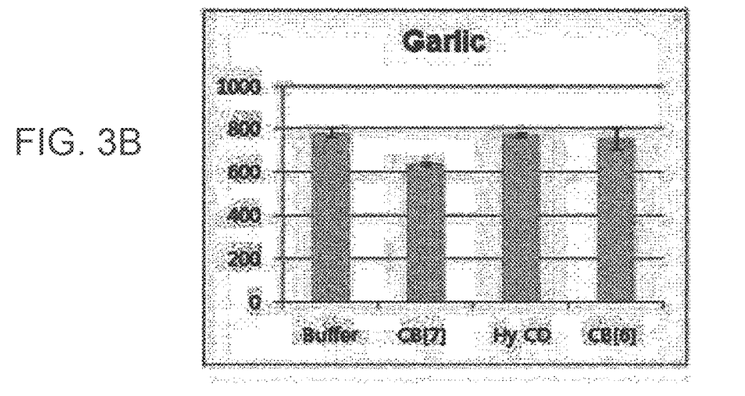
FIG. 3B is a graph showing the effect of removing the odor of garlic using beta-hydroxypropyl cyclodextrin (HY CD, deodorizer) and cucurbituril.
Figure 4B:
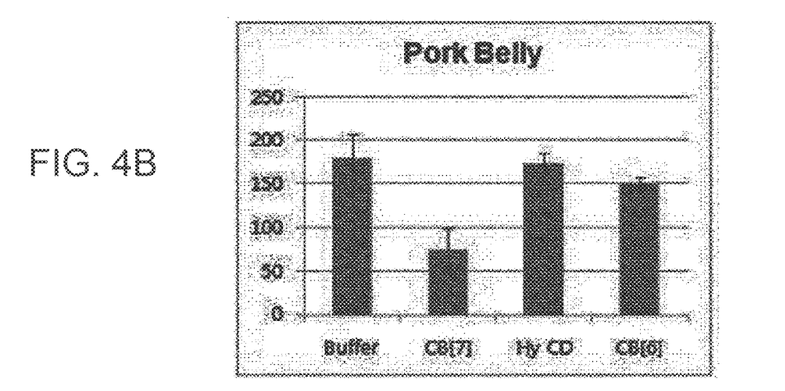
FIG. 4B is a graph showing the effect of removing the odor of pork belly using beta-hydroxypropyl cyclodextrin (HY CD, deodorizer) and cucurbituril.
Figure 5B:
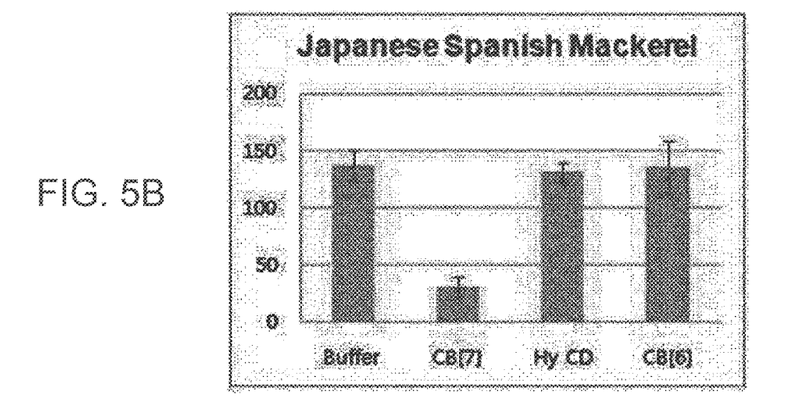
FIG. 5B is a graph showing the effect of removing the odor of a japanese spanish mackerel using beta-hydroxypropyl cyclodextrin (HY CD, deodorizer) and cucurbituril.
Figure 6B:
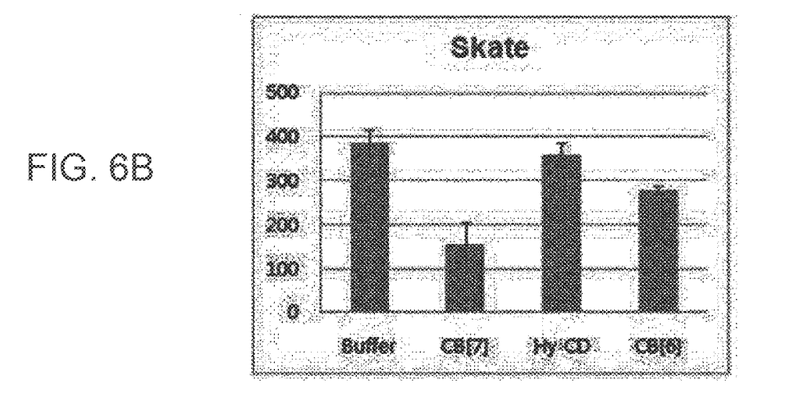
FIG. 6B is a graph showing the effect of removing the odor of a fermented skate using beta-hydroxypropyl cyclodextrin (HY CD, deodorizer) and cucurbituril.

Cucurbit[6]uril (CB[6]), cucurbit[7]uril (CB[7]) and β-hydroxypropyl cyclodextrin (Hy CD) were respectively dissolved in a buffer (PBS, pH 7.2) to obtain a solution (1 w/v %). 1 mL of the solution was sprayed onto odor emission materials such as onion, garlic, pork (pork belly), fish (japanese spanish mackerel), fermented fish (sliced raw skate) and the like. Each of the odor emission materials sprayed with the solution was shaken at a rotation speed of 60 rpm using a shaker machine (N-BIOTEK, ORBITAL SHAKER NB-101S) in order to uniformly disperse the solution, and the degree of odor emission was measured using an odor measuring device (COSMOS, XP-329 m). The results thereof are shown in FIGS. 2B, 3B, 4B, 5B and 6B.

Example 3

Preparation of Odor Removing Composition According to the Kinds of Cucurbituril Homologues and Evaluation of Odor Removing Effect Thereof In order to compare the odor removing effects of cucurbituril homologues with each other, the following experiment was carried out.

Figure 2C:
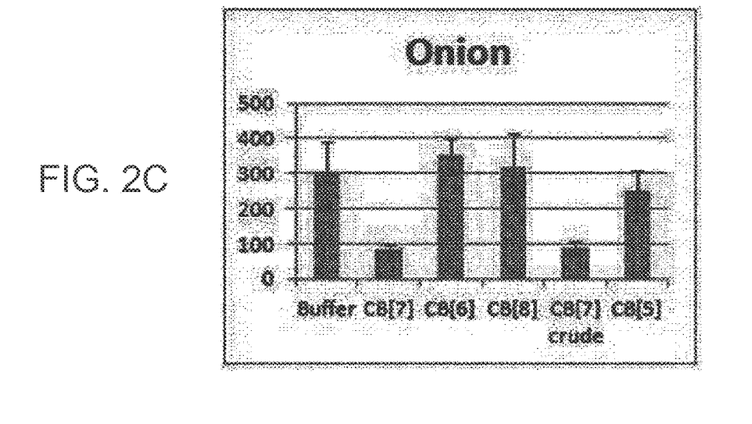
FIG. 2C is a graph showing the effect of removing the odor of onion using cucurbit[5]uril (CB[5]), cucurbit[6]uril (CB[6]), cucurbit[7]uril (CB[7]), cucurbit[8]uril (CB[8]) and crude cucurbit[7]uril (crude (CB[7])
Figure 3C:
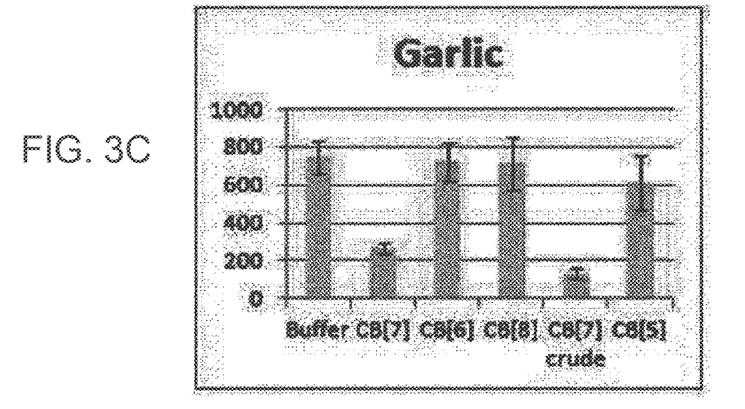
FIG. 3C a graph showing the effect of removing the odor of garlic using cucurbit[5]uril (CB[5]), cucurbit[6]uril (CB[6]), cucurbit[7]uril(CB[7]), cucurbit[8]uril (CB[8]) and crude cucurbit[7]uril (crude (CB[7])
Figure 4C:
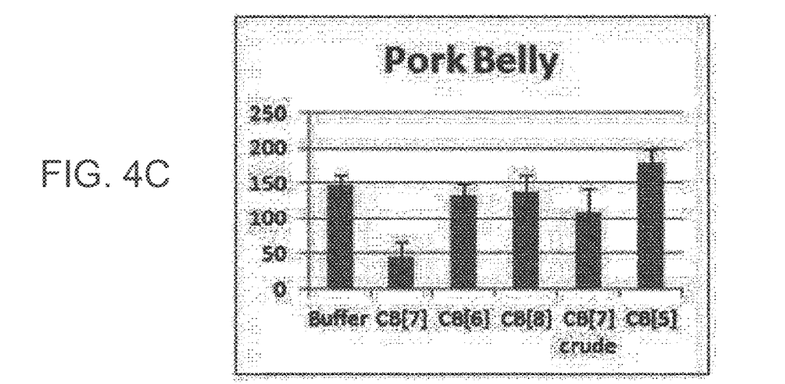
FIG. 4C is a graph showing the effect of removing the odor of pork belly using cucurbit[5]uril (CB[5]), cucurbit[6]uril (CB[6]), cucurbit[7]uril (CB[7]), cucurbit[8]uril (CB[8]) and crude cucurbit[7]uril (crude (CB[7])
Figure 5C:
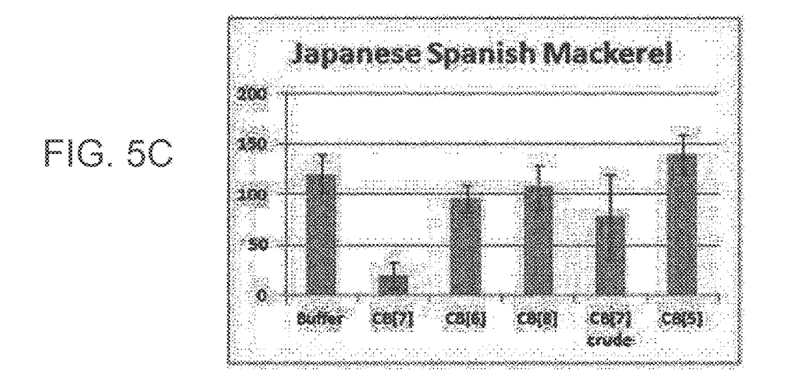
FIG. 5C is a graph showing the effect of removing the odor of a japanese spanish mackerel using cucurbit[5]uril (CB[5]), cucurbit[6]uril (CB[6]), cucurbit[7]uril (CB[7]), cucurbit[8]uril (CB[8]) and crude cucurbit[7]uril (crude (CB[7])
Figure 6C:
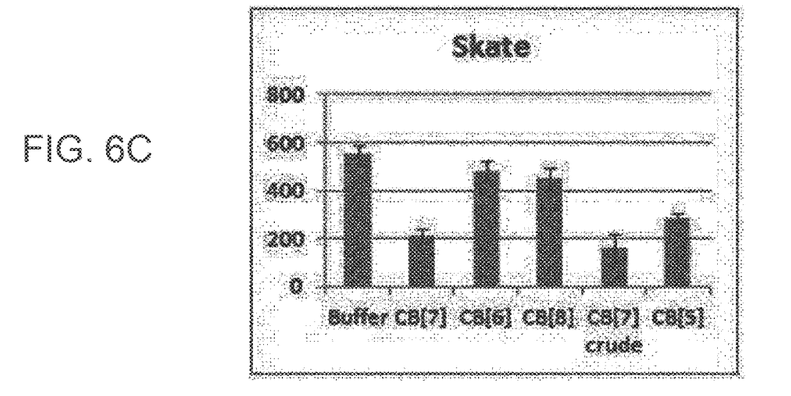
FIG. 6C is a graph showing the effect of removing the odor of a fermented skate using cucurbit[5]uril (CB[5]), cucurbit[6]uril (CB[6]), cucurbit[7]uril (CB[7]), cucurbit[8]uril (CB[8]) and crude cucurbit[7]uril (crude (CB[7]).

Cucurbit[5]uril (CB[5]), cucurbit[6]uril (CB[6]), cucurbit[7]uril (CB[7]), cucurbit[8]uril (CB[8]) and crude cucurbit[7]uril ((crude CB[7]), a complex having a composition ratio of CB7:CB6=2:1) were respectively dissolved in a buffer (PBS, pH 7.2) to obtain a solution (1 w/v %). 1 mL of the solution was sprayed onto odor emission materials such as onion, garlic, pork (pork belly), fish (japanese spanish mackerel), fermented fish (sliced raw skate) and the like. Each of the odor emission materials sprayed with the solution was shaken at a rotation speed of 60 rpm using a shaker machine (N-BIOTEK, ORBITAL SHAKER NB-101S) in order to uniformly disperse the solution, and the degree of odor emission was measured using an odor measuring device (COSMOS, XP-329 m). The results thereof are shown in FIGS. 2C, 3C, 4C, 5C and 6C.

Although the embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The composition can capture and remove various kinds of odor materials (particularly, ammonium ion-containing bad odor, such as a fishy smell or the like) because cucurbituril can interact with various odor materials using its hydrophobic cavity and both inlets covered with carbonyl groups. Therefore, this composition can be practically applied to the cleaning of air and the improvement of an environment.

The invention claimed is:

1. A composition for removing odor, the composition comprising a compound represented by Chemical Formula 1 below:

[Chemical Formula 1]

wherein, n is an integer of 4 to 20, and X is O, S or NH, wherein the composition comprises 45 to 100 wt % of the compound of Chemical Formula 1 of n=7, and wherein the compound of Chemical Formula 1 is dissolved in a buffer.

2. The composition of claim 1, wherein the buffer is selected from the group consisting of PBS (phosphate buffered saline), Tris-HCl, Tricine, HEPES (4-(2-hydroxyethyl)-1-piperazineethanesulfonic acid), MOPS (3-(N-morpholino)propanesulfonic acid), SSC (saline sodium citrate), and MES (2-(N-morpholino)ethanesulfonic acid).

3. The composition of claim 1, further comprising at least one additive selected from the group consisting of ethyl butyrate, camphor, menthol, hexanal, eugenol, citronellol, linalool, patchoulol, santalol, phenyl ethyl alcohol, terpineol, vanillin, benzaldehyde, methyl salicylate, isoamyl acetate, d-limonene, L-limonene, α-pinene, 2-hydroxy-p-cymene, methyl acetophenone, cis-jasmone, cyclohexane, hexane, heptane, isooctane, isopentane, pentane, dimethyl ether, diethyl ether, methanol, ethanol, propanol, isopropanol, butanol, acetone and propellants.

4. The composition of claim 1, wherein the composition captures an odor molecule having an amino group or a carboxyl group.

5. The composition of claim 1, wherein the odor is emitted from an odor emission material selected from onion, garlic, pork, fish, fermented fish, mold, bacteria, body fluids, leather, sewage, and industrial wastewater.

6. The composition of claim 3, wherein the compound is configured to form a complex with an odor molecule having an amino group or carboxyl group.

7. The composition of claim 3, wherein the composition is configured to capture odor from one or more selected from the group consisting of onion, garlic, pork, fish, fermented fish, mold, bacteria, body fluids, leather, sewage and wastewater.

* * * * *